United States Patent
Lee

(10) Patent No.: US 10,568,686 B2
(45) Date of Patent: Feb. 25, 2020

(54) MULTI-ELECTRODE BALLOON CATHETER WITH CIRCUMFERENTIAL AND POINT ELECTRODES

(71) Applicant: Biosense Webster (Israel), Ltd., Yokneam (IL)

(72) Inventor: Christopher Lee, White Plains, NY (US)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 0 days.

(21) Appl. No.: 14/086,791

(22) Filed: Nov. 21, 2013

(65) Prior Publication Data
US 2015/0141982 A1   May 21, 2015

(51) Int. Cl.
*A61B 18/14*   (2006.01)
*A61B 5/00*   (2006.01)
(Continued)

(52) U.S. Cl.
CPC ........ *A61B 18/1492* (2013.01); *A61B 5/6858* (2013.01); *A61B 2017/00327* (2013.01); *A61B 2017/22071* (2013.01); *A61B 2018/0016* (2013.01); *A61B 2018/0022* (2013.01); *A61B 2018/00255* (2013.01); *A61B 2018/00351* (2013.01); *A61B 2018/00357* (2013.01); *A61B 2018/00375* (2013.01); *A61B 2018/00577* (2013.01); *A61B 2018/00839* (2013.01);
(Continued)

(58) Field of Classification Search
CPC ........... A61B 2018/00285; A61B 2018/00255; A61B 2018/0025; A61B 18/1492; A61B 2018/0016; A61B 2018/0022; A61B 2018/00351; A61B 2018/00577; A61B 2019/464; A61B 5/6858
See application file for complete search history.

(56) References Cited

U.S. PATENT DOCUMENTS

| | | | |
|---|---|---|---|
| 4,898,591 A | 2/1990 | Jang et al. | |
| 5,104,393 A | 4/1992 | Isner et al. | |

(Continued)

FOREIGN PATENT DOCUMENTS

| | | |
|---|---|---|
| CN | 103118613 A | 5/2013 |
| CN | 103347456 A | 10/2013 |

(Continued)

OTHER PUBLICATIONS

EPO Partial European Search Report for EP Application No. 14194016.3, dated Mar. 30, 2015, 6 pgs.

(Continued)

*Primary Examiner* — Michael F Peffley
*Assistant Examiner* — Amanda L Zink
(74) *Attorney, Agent, or Firm* — Roberts Calderon Safran & Cole, P.C.

(57) ABSTRACT

A catheter has a balloon electrode assembly with at least one compliant balloon member and at least one electrode carried on an outer surface of the balloon member for accomplishing circumferential sensing or ablation in a tubular region of the heart, including a pulmonary vein or ostium. The catheter may also include an electrode assembly with a tip and/or ring electrode distal of the balloon electrode assembly adapted for focal contact.

24 Claims, 14 Drawing Sheets

(51) Int. Cl.
*A61B 17/22* (2006.01)
*A61B 18/00* (2006.01)
*A61B 17/00* (2006.01)
*A61B 90/00* (2016.01)
*A61B 34/20* (2016.01)

(52) U.S. Cl.
CPC ............... *A61B 2034/2051* (2016.02); *A61B 2034/2053* (2016.02); *A61B 2034/2063* (2016.02); *A61B 2090/065* (2016.02); *A61B 2218/002* (2013.01)

(56) References Cited

U.S. PATENT DOCUMENTS

| | | | |
|---|---|---|---|
| 5,427,119 A | 6/1995 | Swartz et al. | |
| 5,487,385 A | 1/1996 | Avitall | |
| 5,497,119 A | 3/1996 | Tedrow et al. | |
| 5,564,440 A | 10/1996 | Swartz et al. | |
| 5,575,766 A | 11/1996 | Swartz et al. | |
| 5,582,609 A | 12/1996 | Swanson et al. | |
| 5,617,854 A | 4/1997 | Munsif | |
| 5,704,908 A * | 1/1998 | Hofmann | A61N 1/327 604/21 |
| 5,846,238 A | 12/1998 | Jackson et al. | |
| 5,964,757 A | 10/1999 | Ponzi | |
| 6,024,740 A | 2/2000 | Lesh et al. | |
| 6,064,905 A | 5/2000 | Webster, Jr. et al. | |
| 6,117,101 A | 9/2000 | Diederich et al. | |
| 6,142,993 A | 11/2000 | Whayne et al. | |
| 6,251,109 B1 * | 6/2001 | Hassett | A61B 18/1492 606/45 |
| 6,475,213 B1 | 11/2002 | Whayne et al. | |
| 6,540,744 B2 | 4/2003 | Hassett et al. | |
| 6,558,375 B1 | 5/2003 | Sinofsky et al. | |
| 6,692,490 B1 * | 2/2004 | Edwards | A61B 18/1492 606/41 |
| 6,917,834 B2 | 7/2005 | Koblish et al. | |
| 6,973,339 B2 | 12/2005 | Govari | |
| 7,089,063 B2 | 8/2006 | Lesh et al. | |
| 7,189,208 B1 | 3/2007 | Beatty et al. | |
| 7,241,295 B2 | 7/2007 | Maguire | |
| 7,896,870 B2 | 3/2011 | Arless et al. | |
| 7,951,140 B2 | 5/2011 | Arless et al. | |
| 8,083,732 B2 | 12/2011 | Arless et al. | |
| 8,357,152 B2 | 1/2013 | Govari et al. | |
| 8,521,462 B2 | 8/2013 | Govari et al. | |
| 8,535,308 B2 | 9/2013 | Govari et al. | |
| 2002/0065542 A1 * | 5/2002 | Lax et al. | 607/99 |
| 2003/0130713 A1 | 7/2003 | Stewart et al. | |
| 2005/0004507 A1 * | 1/2005 | Schroeppel | A61N 1/05 604/20 |
| 2005/0017152 A1 | 1/2005 | Fergason | |
| 2005/0171525 A1 * | 8/2005 | Rioux | A61B 18/1492 606/41 |
| 2007/0255162 A1 * | 11/2007 | Abboud et al. | 600/547 |
| 2008/0024952 A1 | 1/2008 | Beckwith | |
| 2008/0249522 A1 * | 10/2008 | Pappone et al. | 606/41 |
| 2008/0287860 A1 * | 11/2008 | Tgavalekos | A61B 5/06 604/22 |
| 2009/0093806 A1 | 4/2009 | Govari et al. | |
| 2009/0138007 A1 | 5/2009 | Govari et al. | |
| 2009/0299355 A1 * | 12/2009 | Bencini et al. | 606/21 |
| 2011/0153253 A1 | 6/2011 | Govari et al. | |
| 2012/0014317 A1 | 1/2012 | Rahman | |
| 2012/0143177 A1 * | 6/2012 | Avitall | 606/21 |
| 2013/0066312 A1 * | 3/2013 | Subramaniam et al. | 606/33 |
| 2013/0085493 A1 | 4/2013 | Bloom et al. | |
| 2013/0131743 A1 | 5/2013 | Yamasaki et al. | |
| 2013/0150693 A1 | 6/2013 | D'Angelo et al. | |
| 2013/0158536 A1 * | 6/2013 | Bloom | 606/33 |
| 2013/0197499 A1 | 8/2013 | Lalonde et al. | |
| 2013/0231657 A1 | 9/2013 | Datta et al. | |

FOREIGN PATENT DOCUMENTS

| | | |
|---|---|---|
| EP | 0 661 948 B1 | 11/1997 |
| JP | 2000508220 A | 7/2000 |
| JP | 2010508984 A | 3/2010 |
| JP | 2011524209 A | 9/2011 |
| JP | 2013516218 A | 5/2013 |
| JP | 2013523346 A | 6/2013 |
| WO | WO 93/20767 | 10/1993 |
| WO | 00/42934 A1 | 7/2000 |

OTHER PUBLICATIONS

Extended European Search Report dated Jul. 21, 2015 issued in EP Application No. 14194016.3, 9 pages.
European Office Action issued in Application No. EP14194016.3 dated Feb. 16, 2017, 5 pages.
European Office Action issued in Application No. EP14194016.3 dated Jun. 3, 2016, 4 pages.
European Office Action issued in Application No. EP14194016.3 dated Oct. 31, 2017, 4 pages.
European Office Action issued in Application No. EP15172341.8, dated Jun. 30, 2017, 5 pages.
European Office Action issued in Application No. EP15172341.8, dated Oct. 19, 2016, 4 pages.
Extended European Search Report from Application No. EP15172341. 8, dated Oct. 5, 2015, 6 pages.
Extended European Search Report from Application No. EP17152703. 9, dated Mar. 24, 2017, 7 pages.
Extended European Search Report for European Application No. 18192954.8, dated Nov. 12, 2018, 7 pages.

* cited by examiner

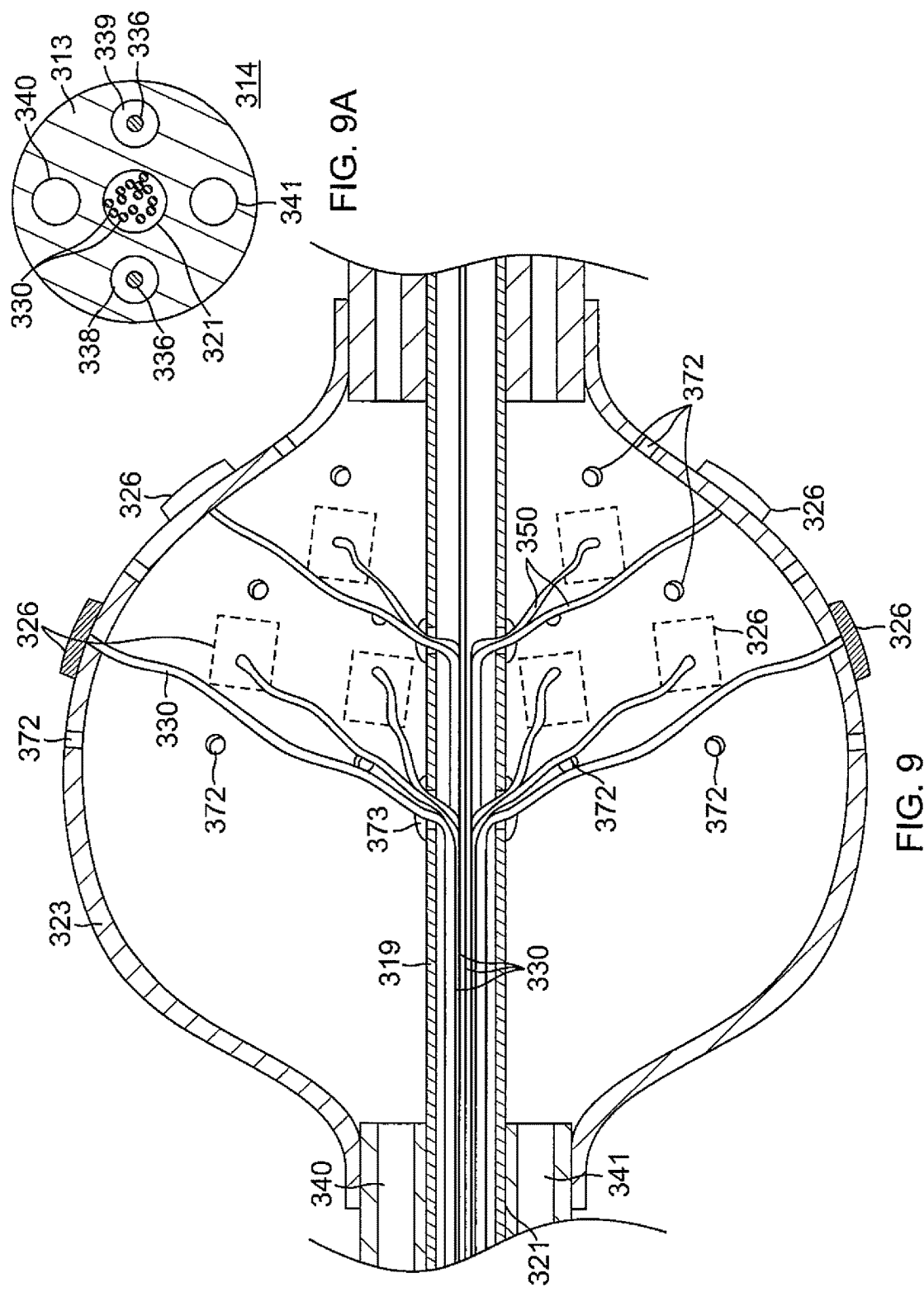

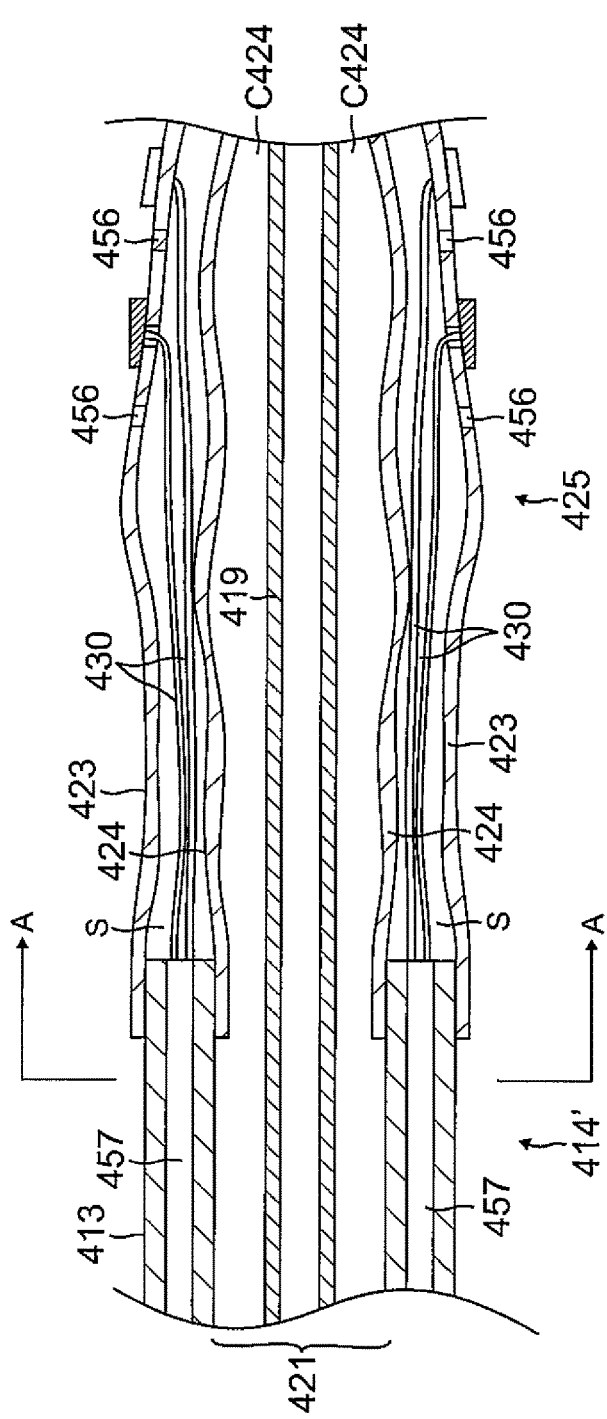
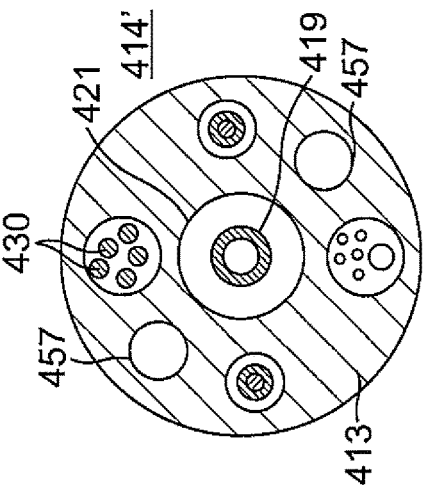
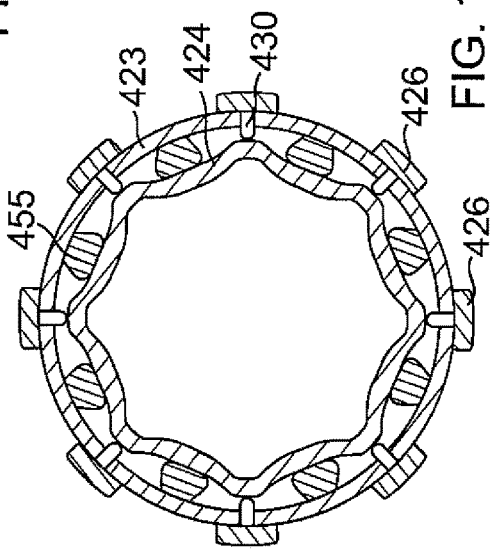
FIG. 10
FIG. 10A
FIG. 10B

MULTI-ELECTRODE BALLOON CATHETER WITH CIRCUMFERENTIAL AND POINT ELECTRODES

FIELD OF INVENTION

This invention relates to electrophysiologic (EP) catheters, in particular, EP catheters for mapping and/or ablation in the heart.

BACKGROUND

Cardiac arrhythmias, and atrial fibrillation in particular, persist as common and dangerous medical ailments, especially in the aging population. In patients with normal sinus rhythm, the heart, which is comprised of atrial, ventricular, and excitatory conduction tissue, is electrically excited to beat in a synchronous, patterned fashion. In patients with cardiac arrhythmias, abnormal regions of cardiac tissue do not follow the synchronous beating cycle associated with normally conductive tissue in patients with sinus rhythm. Instead, the abnormal regions of cardiac tissue aberrantly conduct to adjacent tissue, thereby disrupting the cardiac cycle into an asynchronous cardiac rhythm. Such abnormal conduction has been previously known to occur at various regions of the heart, for example, in the region of the sino-atrial (SA) node, along the conduction pathways of the atrioventricular (AV) node and the Bundle of His, or in the cardiac muscle tissue forming the walls of the ventricular and atrial cardiac chambers.

Cardiac arrhythmias, including atrial arrhythmia, may be of a multiwavelet reentrant type, characterized by multiple asynchronous loops of electrical impulses that are scattered about the atrial chamber and are often self propagating. In the alternative or in addition to the multiwavelet reentrant type, cardiac arrhythmias may also have a focal origin, such as when an isolated region of tissue in an atrium fires autonomously in a rapid, repetitive fashion.

A host of clinical conditions may result from the irregular cardiac function and resulting hemodynamic abnormalities associated with atrial fibrillation, including stroke, heart failure, and other thromboembolic events. In fact, atrial fibrillation is believed to be a significant cause of cerebral stroke, wherein the abnormal hemodynamics in the left atrium caused by the fibrillatory wall motion precipitate the formation of thrombus within the atrial chamber. A thromboembolism is ultimately dislodged into the left ventricle, which thereafter pumps the embolism into the cerebral circulation where a stroke results. Accordingly, numerous procedures for treating atrial arrhythmias have been developed, including pharmacological, surgical, and catheter ablation procedures.

Examples of catheter-based devices and treatment methods have generally targeted atrial segmentation with ablation catheter devices and methods adapted to form linear or curvilinear lesions in the wall tissue which defines the atrial chambers, such as those disclosed in U.S. Pat. No. 5,617,854 to Munsif, U.S. Pat. No. 4,898,591 to Jang et al., U.S. Pat. No. 5,487,385 to Avitall, and U.S. Pat. No. 5,582,609 to Swanson, the disclosures of which are incorporated herein by reference. The use of particular guiding sheath designs for use in ablation procedures in both the right and/or left atrial chambers are disclosed in U.S. Pat. Nos. 5,427,119, 5,497,119, 5,564,440, and 5,575,766 to Swartz et al., the disclosures of which are incorporated herein by reference.

Less-invasive percutaneous catheter ablation techniques have been disclosed which use end-electrode catheter designs with the intention of ablating and thereby treating focal arrhythmias in the pulmonary veins. These ablation procedures are typically characterized by the incremental application of electrical energy to the tissue to form focal lesions designed to interrupt the inappropriate conduction pathways. Focal ablation methods are intended to destroy and thereby treat focal arrhythmia originating from a pulmonary vein.

U.S. Pat. No. 6,973,339 discloses a lasso catheter for pulmonary vein mapping and ablation. The apparatus for circumferentially mapping a pulmonary vein (PV) comprises a catheter that includes a curved section of a known fixed length, preferably shaped to generally conform to the shape of the interior surface of the PV. The curved section comprises one or more sensing electrodes, and its proximal end is joined at a fixed or generally known angle to a base section of the catheter, or at an angle whose range is limited. Preferably, at least one single-coil five-dimensional position sensors is fixed to the curved section of the catheter. Most preferably, two single-coil five-dimensional position sensors are fixed to the curved section, one at the distal end and one approximately at the center of the curve. A multi-coil six-dimensional position sensor is preferably fixed to the distal end of the base section, proximate to the joint with the curved section. The catheter is inserted into the heart, and the curved section is positioned in essentially continuous contact with the wall of the PV, while the base section remains within the left atrium, typically positioned such that the joint with the curved section is at the ostium of the vein. The information generated by the three position sensors is used to calculate the locations and orientations of the sensing electrodes, which enables mapping of the surface of the PV.

U.S. Pat. Nos. 6,024,740 and 6,117,101 disclose a circumferential ablation device assembly which is adapted to forming a circumferential conduction block in a pulmonary vein. The assembly includes a circumferential ablation element which is adapted to ablate a circumferential region of tissue along a pulmonary vein wall which circumscribes the pulmonary vein lumen, thereby transecting the electrical conductivity of the pulmonary vein against conduction along its longitudinal axis and into the left atrium. The circumferential ablation element includes an expandable member with a working length that is adjustable from a radially collapsed position to a radially expanded position. An equatorial band circumscribes the outer surface of the working length and is adapted to ablate tissue adjacent thereto when actuated by an ablation actuator. The equatorial band has a length relative to the longitudinal axis of the expandable member that is narrow relative to the working length, and is also substantially shorter than its circumference when the working length is in the radially expanded position. A pattern of insulators may be included over an ablation element which otherwise spans the working length in order to form the equatorial band described. The expandable member is also adapted to conform to the pulmonary vein in the region of its ostium, such as by providing a great deal of radial compliance or by providing a taper along the working length which has a distally reducing outer diameter. A linear ablation element is provided adjacent to the circumferential ablation element in a combination assembly which is adapted for use in a less-invasive "maze"-type procedure in the region of the pulmonary vein ostia in the left ventricle.

In addition, various energy delivery modalities have been disclosed for forming such atrial wall lesions, and include use of microwave, laser, and more commonly, radiofrequency energies to create conduction blocks along the cardiac tissue wall, as disclosed in WO 93/20767 to Stem et al., U.S. Pat. No. 5,104,393 to Isner et al., and U.S. Pat. No. 5,575,766 to Swartz et al, respectively, the disclosures of which are incorporated herein by reference. U.S. Pat. No. 6,558,375 to Sinofsky, et al., discloses a hand held cardiac ablation instrument and methods for irradiating a target ablation site. The instrument can include at least one light transmitting optical fiber and a light diffusing element to create a circumferential or curvilinear lesion. Light travelling through the light transmitting optical fiber or fibers is scattered in a circular pattern by the light diffusing element. The light diffusing element can include a scattering medium, a reflective end cap, and a reflective surface diametrically opposed to the target ablation site, that interact to provide a substantially uniform distribution of laser radiation throughout the circular target region.

Ablation with cryogens is also known. U.S. Pat. Nos. 7,896,870; 7,951,140 and 8,083,732, each to Arless, et al., disclose catheters having a cryoablation tip with an electrically-driven ablation assembly for heating tissue. The cryoablation tip may be implemented with a cooling chamber through which a controllably injected coolant circulates to lower the tip temperature, and having an RF electrode at its distal end. The RF electrode may be operated to warm cryogenically-cooled tissue, or the coolant may be controlled to conductively cool the tissue in coordination with an RF treatment regimen.

Regardless of the type of catheter used, it is emphasized that particular care must be exercised to ensure that the ablation sites are indeed contiguous; otherwise irregular electrical activity in the pulmonary vein may continue to contribute to atrial arrhythmia. Thus, where ablation of a pulmonary vein has been performed whether with a balloon or lasso catheter or otherwise, a subsequent PV isolation validation often reveals locations or points that have been missed. Typically, a point ablation catheter would then be used to complete the isolation.

Catheters with pressure sensing for detecting tissue contact, facilitating in lesion formation and avoiding perforation of tissue are known. Such catheters may carry a miniature transmitting coil and multiple sensing coils on opposing portions of a flexibly-jointed distal tip section. This design is well-suited for point ablation catheters, but does not lend itself to catheters adapted for tissue contact over an area or at multiple locations, such as with a coil or "lasso" catheter having a distal electrode assembly with a generally circular portion. For these catheters, because the generally circular portion is transverse to the catheter body, the generally circular portion may not exert uniform pressure along its length when an operator applies a distal force on the catheter body to ensure contact between with tissue and the electrodes on the generally circular portion. In particular, the electrodes closer to the catheter body tend to exert greater pressure against the tissue.

Accordingly, each type of catheter has its advantages and disadvantages. Point ablation catheters have distal tip electrodes better suited for point ablation but are time and labor intensive for when ablating larger regions. Circumferential ablation catheters may require less operator skill and less time by enabling multiple contact points simultaneously but they may not easily adapt to variations in anatomy between individual patients. Consequently, a single procedure may require the use of at least two or three catheters for mapping, ablation and electrical/anatomical isolation validation which can significantly increase the cost of the procedure and the duration.

Thus, there is a desire for an electrophysiologic catheter that can provide both point and circumferential mapping and ablation. It is desirable that the catheter have a distal tip electrode for point tissue contact and be capable of adopting a radially expanded configuration for circumferential tissue contact. Moreover, it is desirable that the catheter have improved pressure sensing capabilities to accommodate two- and three-dimensional electrode assemblies with multiple electrode contact points.

SUMMARY OF THE INVENTION

The present invention is directed to a catheter with a balloon electrode assembly with at least one compliant balloon member and at least one electrode carried on an outer surface of the balloon member for accomplishing circumferential sensing or ablation in a tubular region of the heart, including a pulmonary vein or ostium. The catheter may also include an electrode assembly with a tip and/or ring electrode distal of the balloon electrode assembly adapted for focal contact.

The balloon electrode assembly remains deflated as the catheter is advanced through the patient's body to the desired location in the heart. The balloon electrode assembly may remain deflated as the heart is mapped. The balloon electrode assembly may then be inflated to a desirable circumference/size and inserted into an ostium of a pulmonary vein. The balloon electrode assembly is adapted to sit in the ostium with its electrodes making contact with tissue along a circumference. The EP operator may ablate, rotate the assembly, ablate, etc., until generally all points along the circumference have been ablated to isolate the pulmonary vein. Each pulmonary vein may be isolated in this manner. The balloon electrode assembly may then be deflated and the distal electrode assembly with focal point contact used to validate the isolation. In that regard, the distal electrode assembly may be used for touch-ups, roofline, CFAE or other RF ablation strategies in more complicated cases. The multi-functionality of the catheter advantageously streamline workflow, reducing the number of different catheters that would otherwise be used in the atria. The balloon electrode assembly provides operators with a greater certainty of electrode placement in the pulmonary veins, while the distal electrode assembly enables focal point treatment by the same catheter.

In one embodiment, the catheter includes an elongated catheter body, a first assembly distal of the catheter body with at least one balloon member with an outer surface and at least one electrode on the outer surface, and a second assembly distal of the first assembly, the second assembly having at least one electrode. The catheter also includes a tubing extending through the catheter body, where the tubing defines a lumen adapted to pass fluid into the at least one balloon member to expand the at least one balloon member.

In a detailed embodiment, the catheter further includes a pressure sensing assembly, and the pressure sensing assembly may be located proximal of the at least one balloon member, or between a distal end and a proximal end of the at least one balloon member.

In a detailed embodiment, the at least one balloon member has at least one fluid port configured to allow fluid to pass from inside to outside the balloon member.

In a detailed embodiment, the catheter further includes a second outer balloon member configured to cover at least a portion of the at least one balloon member.

In a detailed embodiment, the at least one electrode is elongated and positioned along a longitudinal axis of the catheter. The at least one electrode of the second assembly includes an irrigated tip electrode or a ring electrode.

In an alternate embodiment, the catheter comprises an elongated catheter body, a balloon electrode assembly distal of the catheter body, and a tubing extending through the catheter body. The balloon electrode assembly has at least an inner balloon member and an outer balloon member covering at least a portion of the inner balloon member, and at least one electrode on an outer surface of the outer balloon member. The tubing defines a lumen adapted to pass fluid into the inner balloon member for expansion of the inner balloon member. The outer balloon member is adapted for expansion in response to expansion of the inner balloon member.

In a detailed embodiment, the catheter includes a distal electrode assembly distal of the balloon electrode assembly.

In a detailed embodiment, the inner balloon member has at least one fluid port configured to pass fluid from inside the inner balloon member to a space outside of the inner balloon member covered by the outer balloon member. The outer balloon member has at least one fluid port configured to pass fluid from the space to outside of the outer balloon member.

In a detailed embodiment, the catheter includes a pressure sensing assembly with a resilient member that is responsive to contact pressure on the balloon electrode assembly.

BRIEF DESCRIPTION OF THE DRAWINGS

These and other features and advantages of the present invention will be better understood by reference to the following detailed description when considered in conjunction with the accompanying drawings wherein:

FIG. 9 is a side cross-sectional view of a balloon electrode assembly of the present invention, in accordance with another embodiment.

FIG. 9A is an end cross-sectional view of an embodiment of an intermediate deflectable section suitable for use with the balloon electrode assembly of FIG. 9.

FIG. 10 is a side cross-sectional view a catheter of the present invention, in accordance with another embodiment, taken along a first diameter.

FIG. 10A is an end cross-sectional view of the intermediate deflectable section of FIG. 10, taken along line A-A.

FIG. 10B is an end cross-sectional view of balloon members of an intermediate deflectable section, with spacers, in accordance with another embodiment of the present invention.

DETAILED DESCRIPTION OF THE INVENTION

Figure 1:
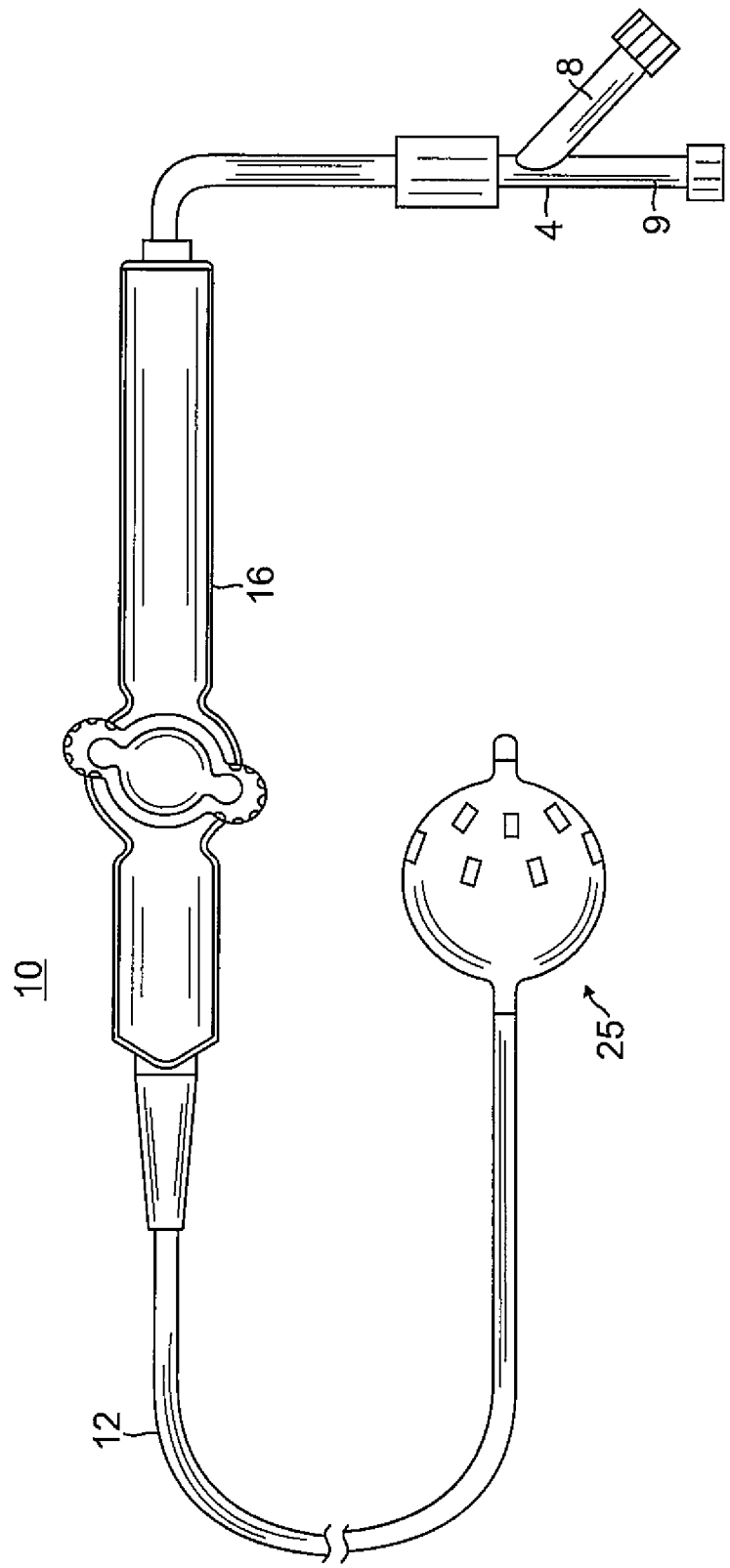
FIG. 1 is a perspective view of a catheter of the present invention, in accordance with one embodiment.

With reference to FIG. 1, the invention is directed to a catheter 10 having a balloon electrode assembly 25 that can inflate and deflate as needed for mapping and/or ablation of a tubular region of the heart, including a pulmonary vein of the left atrium.

The catheter 10 comprises an elongated catheter body 12, a control handle 16 at a proximal end of the catheter body 12, and the balloon electrode assembly 25 at the distal end of the catheter body 12.

Figure 2:
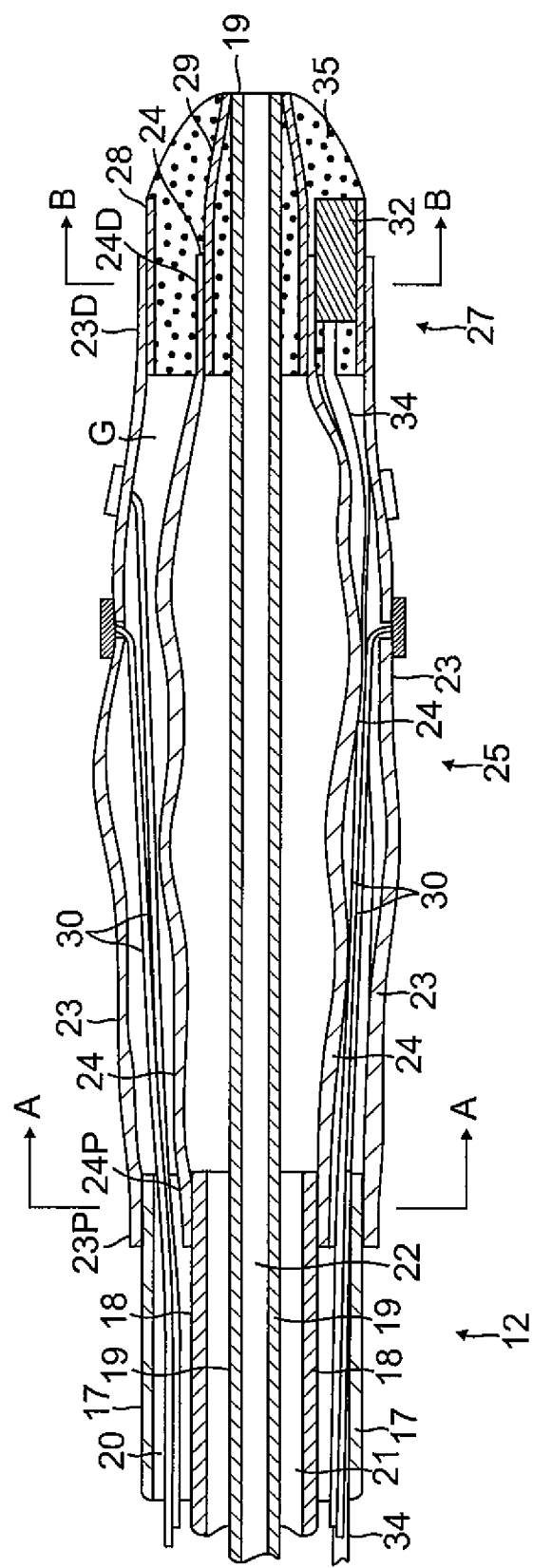
FIG. 2 is a side cross-sectional view of a balloon electrode assembly and a distal tip section of the catheter of FIG. 1, in a deflated/collapsed configuration.
Figure 2B:
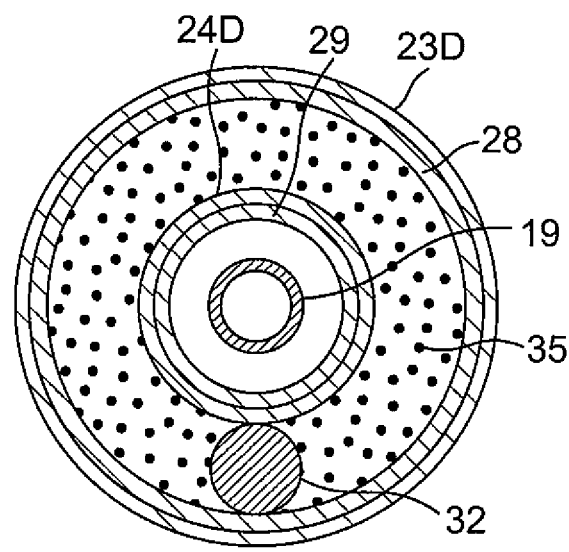
FIG. 2B is an end cross-sectional view of the distal tip section of FIG. 2, taken along line B-B.
Figure 2A:
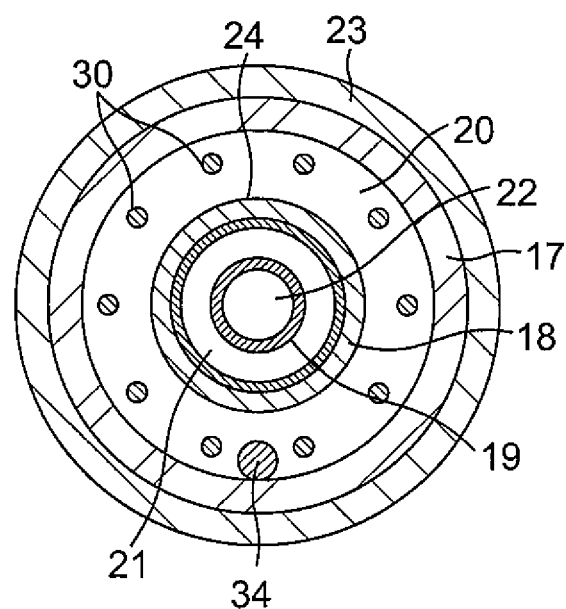
FIG. 2A is an end cross-sectional view of the balloon electrode assembly of FIG. 2, taken along line A-A.

As shown in FIGS. 2 and 2A, the catheter body 12 comprises an elongated tubular construction having an outer tube 17 with a single lumen 20, an inner tube 18 with a single lumen 21, and a guidewire tube 19 with a guide wire lumen 22. The tubes 17, 18 and 19 are coaxial, with the inner tube 18 extending through the lumen 20 of the outer tube 17, and the guidewire tube 19 extending through the lumen 21 of the inner tube 18. The tubes 17, 18 and 19 are flexible, i.e., bendable, but substantially non-compressible along its length. The tubes may be of any suitable construction and made of any suitable material. In one embodiment, the tubes, 17, 18 and 19 are constructed of polyurethane or PEBAX® (polyether block amide). The outer tube 17 may further comprise an imbedded braided mesh of stainless steel or the like to increase torsional stiffness of the catheter body 12 so that, when the control handle 16 is rotated, the distal end of the catheter body 12 will rotate in a corresponding manner.

As shown in FIG. 1, proximal of the control handle 16, a connecting member or hub 4 has been affixed to the inner tube 18 and the guidewire tube 19, each of which has a proximal portion that extends proximally of the control handle. The connecting member 4 has ports 8 and 9 which connect, respectively, with the lumen 21 of the inner tube 18 and the lumen 22 of the guidewire tube 19. The port 8 is adapted for connection with a pressurizeable fluid source and a pump (not shown). The port 9 is adapted for receiving a guidewire (not shown).

The outer diameter of the catheter body 12 is not critical. In one embodiment, the outer diameter is no more than about 8 french, more preferably 7 french. Likewise the thickness of each tube is not critical, so long as each lumen provides a sufficient gap of space between each tube to accommodate components and/or substances in between. As shown in FIGS. 2 and 2A, components that extend through the lumen 20 between the outer tube 17 and the inner tube 18 include lead wires 30 for electrodes and a cable 28 for an electromagnetic position sensor 32 housed in or near the assembly 25. Another component may be a thermocouple wire pair (not shown). A substance that flows through the lumen 21 between the inner tube 18 and the guidewire tube 19 is an inflation medium, e.g., saline, for expanding the balloon assembly 25.

The useful length of the catheter body 12 that can be inserted into a patient's body excluding the assembly 25, can vary as desired. In one embodiment, the useful length ranges from about 110 cm to about 120 cm, more preferably about 115 cm to about 117 cm, and still more preferably about 116 cm.

Figure 4:
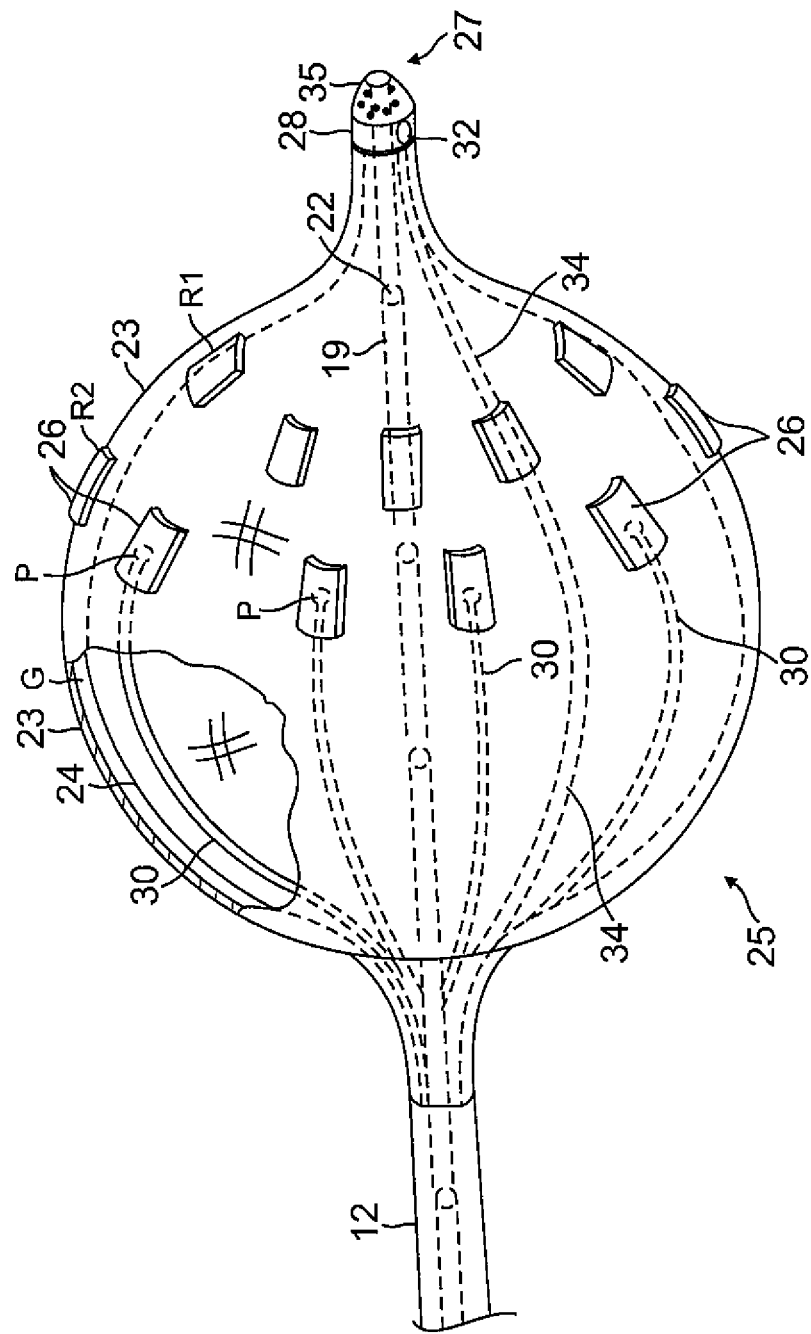
FIG. 4 is a perspective view of the expanded/inflated balloon electrode assembly of FIG. 1.

With reference to FIGS. 2 and 4, at a distal end of the catheter body 12 is the balloon electrode assembly 25. The balloon electrode assembly 25 includes at least a pair of generally similarly shaped and sized outer balloon member 23 and inner balloon member 24, a plurality of electrodes 26 mounted on an outer surface of the outer balloon member 23. A distal assembly 27 extends from a distal end of the balloon electrode assembly 25. In the illustrated embodiment, the distal assembly includes an outer ring or tube 28, an inner ring or tube 29, and a location sensor 32 housed in the distal assembly between the rings 28 and 29. The cable 34 attached to the sensor 32 extends in gap G between the inner and outer balloon members 24 and 23. A distal end of the guidewire tube 19 extends through the inner ring 29 and is coextensive with a distal end of the inner ring 29. Glue 35 is applied to the distal assembly 27 to hold the distal assembly together. The glue is formed into an atraumatic end around the distal end of the guidewire tube 19. To that end, the distal end of the ring 28 and/or ring 29 may be tapered.

Figure 3:
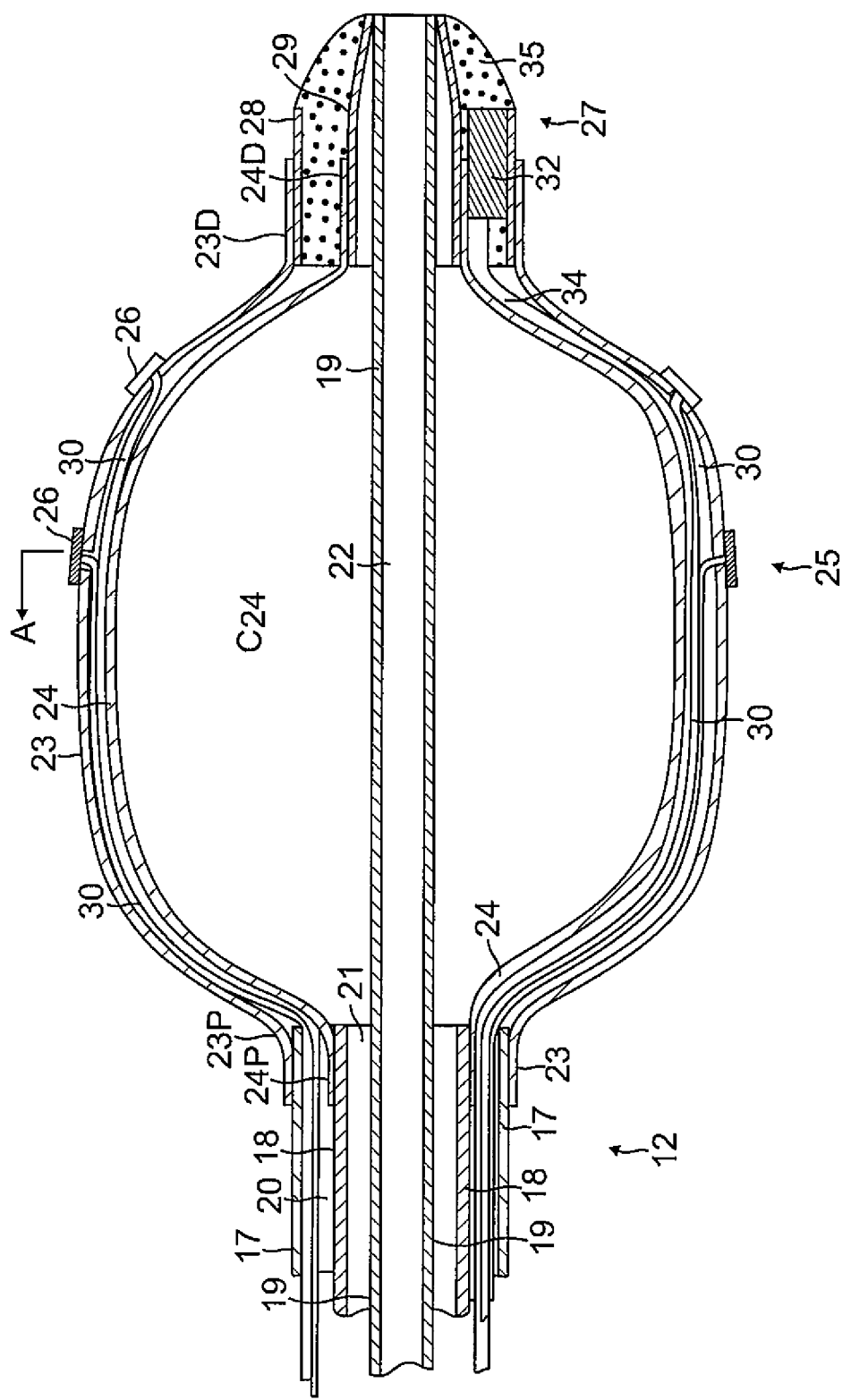
FIG. 3 is a side cross-sectional view of the balloon electrode assembly of FIG. 2, in an expanded/inflated configuration.
Figure 3A:
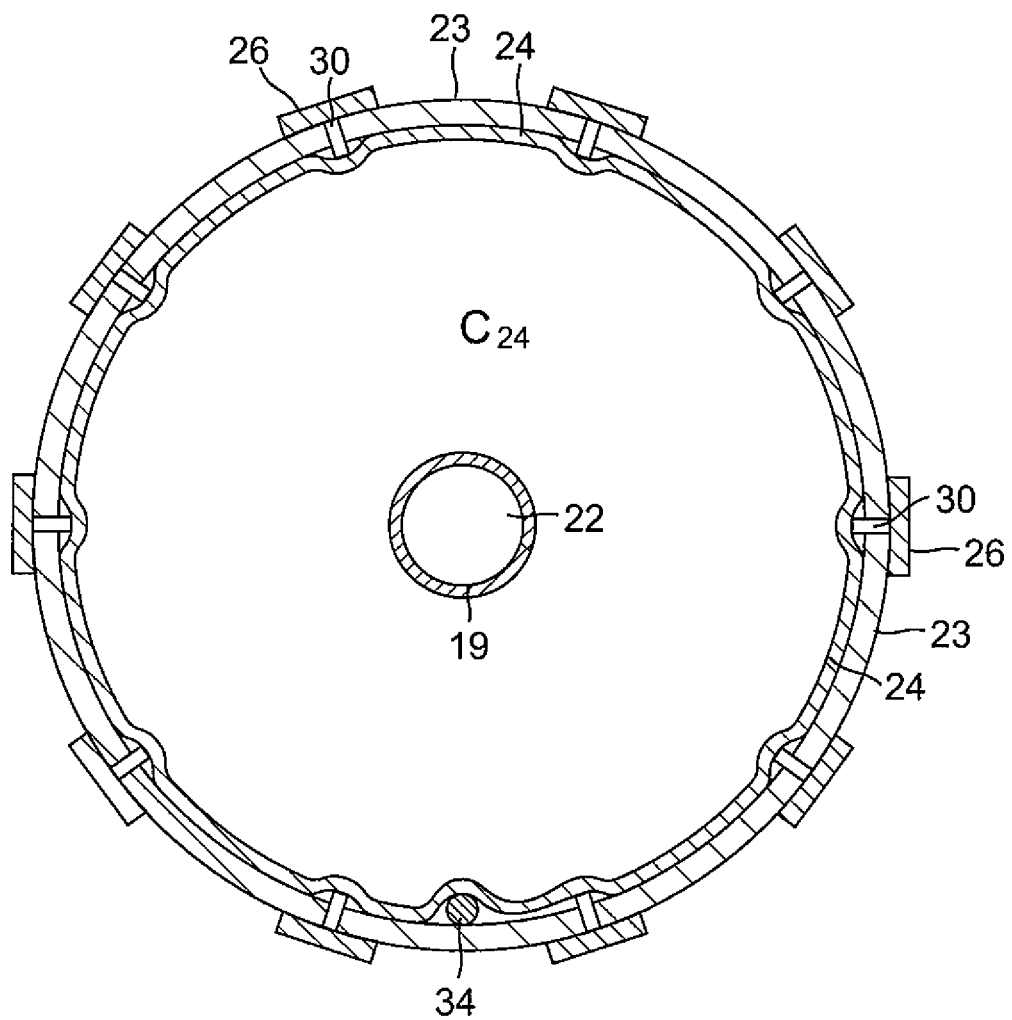
FIG. 3A is an end cross-sectional view of the balloon electrode assembly of FIG. 3, taken along line A-A.

With reference to FIGS. 2, 3 and 3A, each of the balloon members 23 and 24 is generally tubular with a proximal opening, a distal opening and a cavity C23 and C24 therebetween. The inner balloon member 24 is slightly smaller than the outer balloon member 25 so that the inner balloon member fits inside the outer balloon member 23 but nevertheless when inflated is able to apply an outward force to expand the outer balloon member. It is understood that the terms "expand" and "inflate" are used interchangeably herein, as are the terms "collapse" and "deflate." The inner balloon member 24 is mounted over a distal portion of the guidewire tube 19 that extends distally from the catheter body 12. The member 24 thus surrounds the distal portion of the guidewire tube 19 which extends through the cavity C24 of the inner balloon member 24 between its proximal opening 24P and distal opening 24D. Proximal opening 24P is mounted and sealed around an outer surface of a distal end of the inner tube 18. Distal opening 24D is mounted on and sealed around an outer surface of a proximal end of the inner ring 29 of the distal assembly 27.

The outer balloon member 23 is mounted over the inner balloon member 24 such that the inner balloon member 24 is situated inside and is surrounded by the outer balloon 23. A proximal opening 23P is mounted and sealed around an outer surface of a distal end of the outer tubing 17. A distal opening 23D is mounted and sealed around an outer surface of a proximal end of the outer ring 28 of the distal assembly 27.

With reference to FIG. 4, the electrodes 26 are arranged in at least one circumferential row radially around the outer balloon member 23, each electrode being equally spaced from adjacent electrodes in the row. In the illustrated embodiment, the electrodes are arrange generally on a distal half of the outer balloon member 23, in two or more circumferential rows, with adjacent rows R1 and R2 being radially offset or staggered from each other. In one embodiment, row R2 has nine electrodes and row R1 has at least nine electrodes, and more preferably three or four electrodes.

Each electrode is affixed, deposited or otherwise mounted to the outer surface of the outer balloon member 23 and connected to a respective lead wire 30 through a puncture or aperture P in the side wall of the member 23. Each lead wire 30 extends distally from the catheter body 12 toward its respective electrode through the gap G between the outer balloon member 23 and the inner balloon member 24.

The balloon members 23 and 24 are constructed of a flexible, compliant material, which can be elastic or inelastic, that allows the members to inflate and expand outwardly under an internal force (FIG. 2) and to deflate and collapse when the force is absent or removed (FIG. 3). The internal force is provided by introduction of the inflation medium into cavity C24 of the inner balloon member 24. The port 8 (FIG. 1) is connected to a pressurizeable fluid or inflation medium source and a pump (not shown) which delivers the inflation medium into the port 8 and through the lumen 21 of the inner tube 18 in the space between the inner tube 18 and the guidewire tube 19. The inner tube 18 and the guidewire tube 19 are relatively sized to allow the inflation medium to flow sufficiently unimpeded along the length of the catheter. The inflation medium passes through the catheter body 12 and enters the cavity C23 of the inner balloon member 23 to expand the inner balloon member, which in turn, expands the outer balloon member 24. The inflation medium may also be drawn out of the cavity C23 via the lumen 21 by reversing the pump, to deflate the balloon members 23 and 24.

Figure 5:
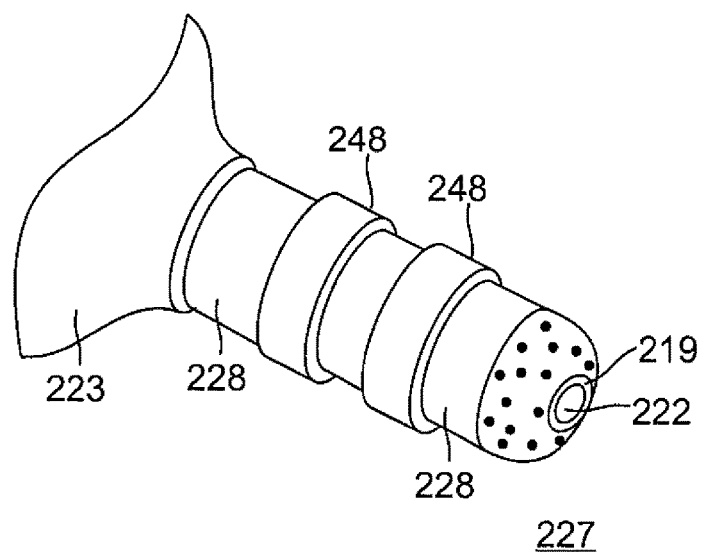
FIG. 5 is a perspective view of a distal electrode assembly of the present invention, in accordance with one embodiment.
Figure 5A:
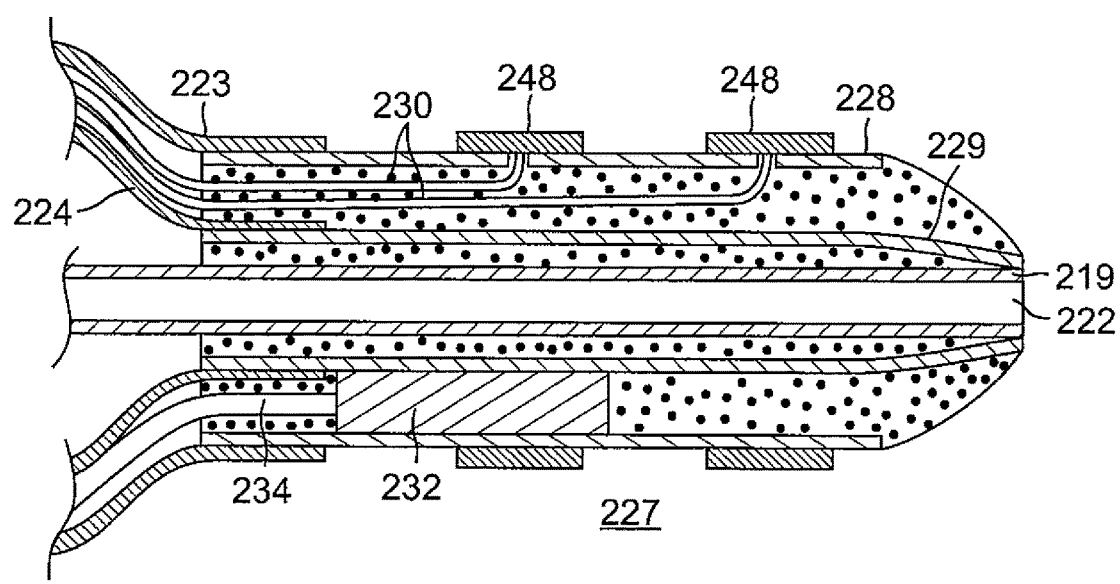
FIG. 5A is a side cross-sectional view of the distal electrode assembly of FIG. 5.

FIGS. 5 and 5A illustrate a distal assembly 227 in accordance with another embodiment. The distal assembly 227 has a structure similar to the distal assembly 27 of FIGS. 2 and 3, as described above. However, one difference is the ring electrode(s) 248 carried on the distal assembly 227. In the distal assembly 227, outer ring 228 has a sufficient length to carry at least one ring electrode 248 distal of balloon assembly 225. In the illustrated embodiment, the outer ring 228 carries two ring electrodes, each of which is connected to a respective lead wire 230 that extends between the outer ring 228 and inner ring 229, and more proximally between inner and outer balloon members 223 and 224. The inner ring 229 may also have an increased length to help support the distal assembly 227. A location sensor 232 and its cable 234 are positioned between the rings 228 and 229.

Figure 6A:
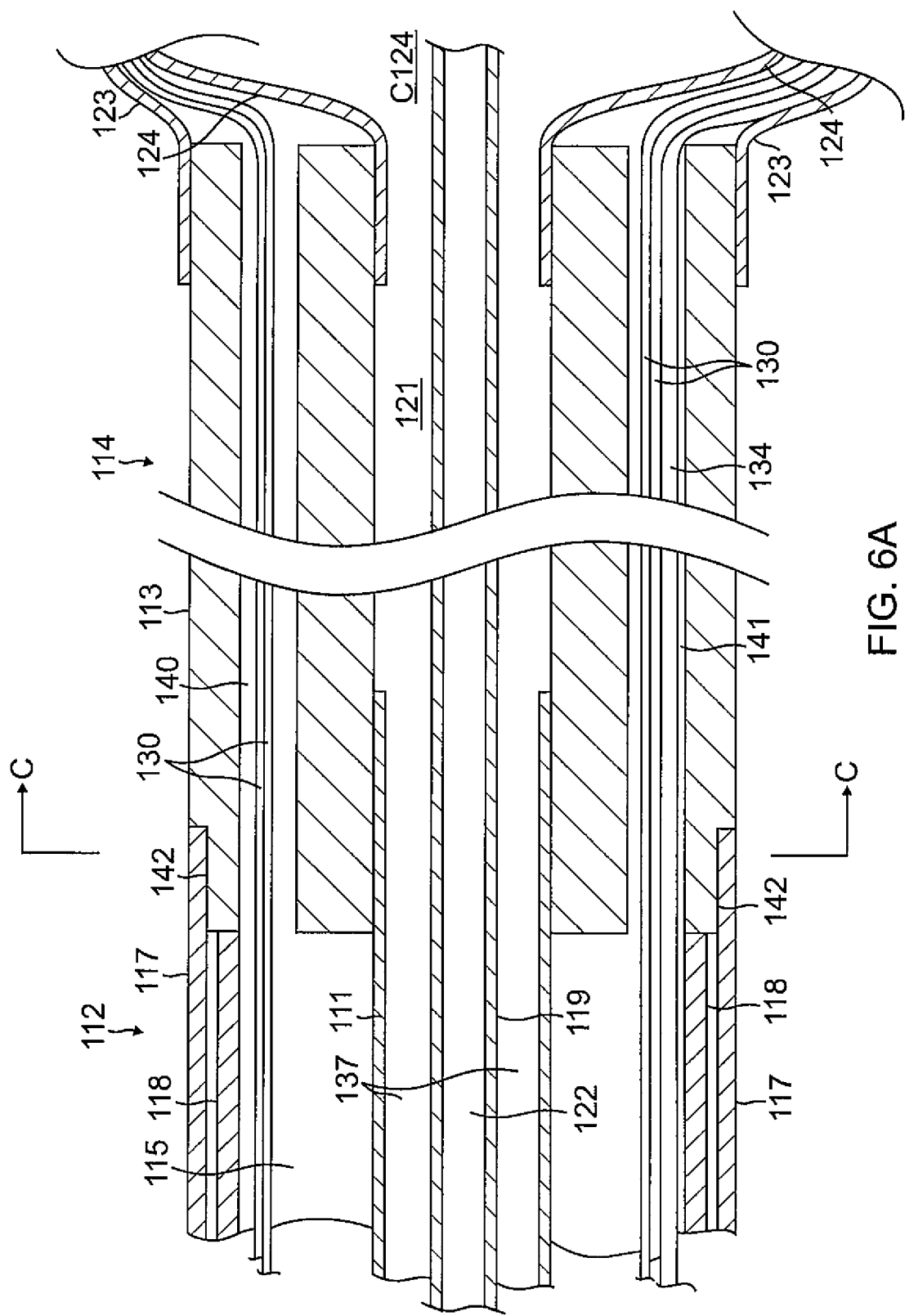
FIG. 6A is a side cross-sectional view of a catheter of the present invention, having an intermediate deflectable section, in accordance with another embodiment, taken along a first diameter.
Figure 6B:
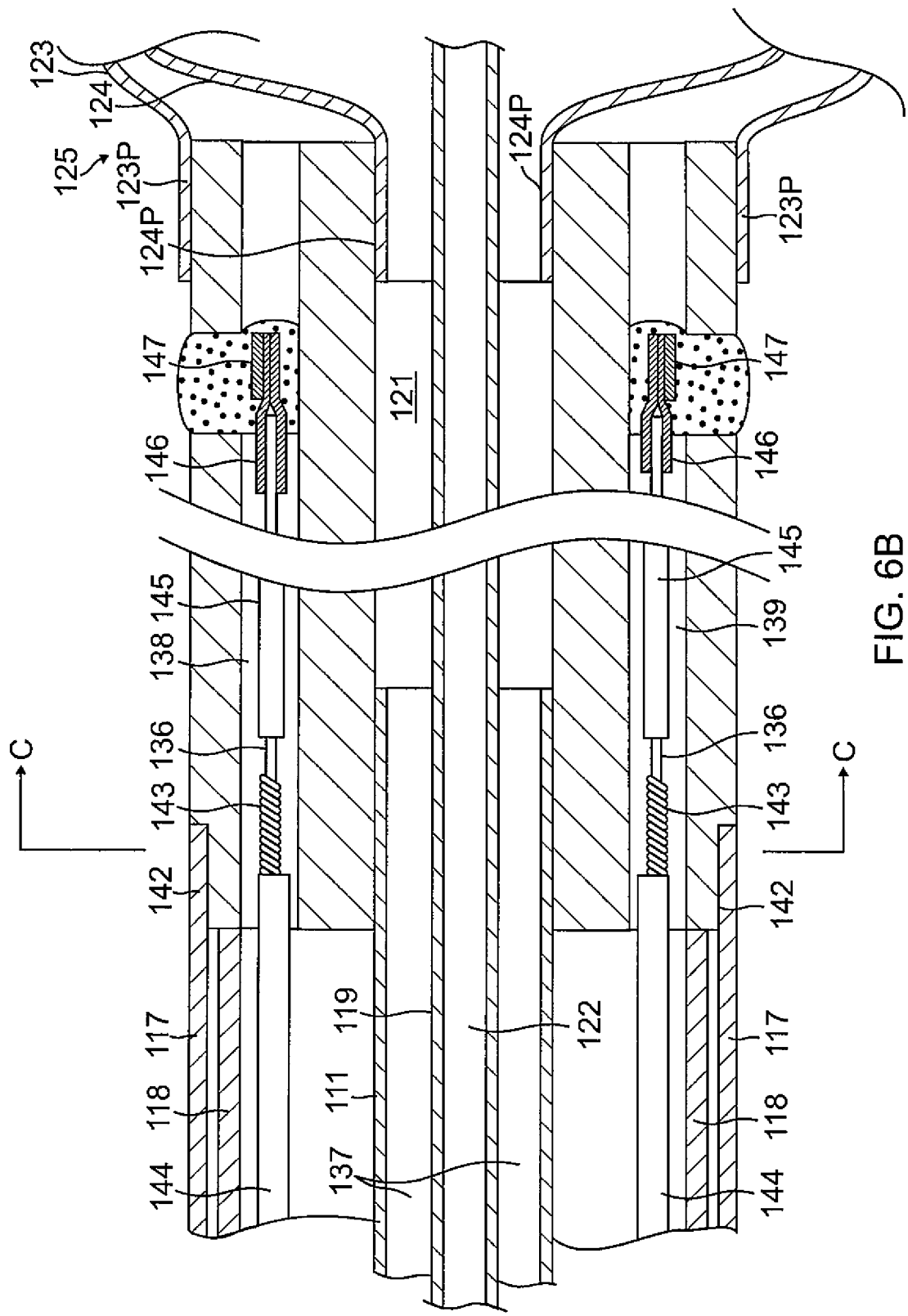
FIG. 6B is a side cross-sectional view of the catheter of FIG. 6A taken along a second diameter generally perpendicular to the first diameter.

As shown in FIGS. 6A and 6B, a catheter body 112 of another embodiment comprises an elongated tubular construction having a single, axial or central lumen 115. The catheter body 112 is flexible, i.e., bendable, but substantially non-compressible along its length. The catheter body 112 can be made of any suitable construction and made of any suitable material. One construction is of polyurethane or PEBAX® (polyether block amide). The catheter body 112 includes an outer wall 117 comprising an imbedded braided mesh of stainless steel or the like to increase torsional stiffness of the catheter body 112 so that, when a control handle (not shown) is rotated, the distal end of the catheter body 112 will rotate in a corresponding manner.

The outer diameter of the catheter body 112 is not critical. In one embodiment, the outer diameter is no more than about 8 french, more preferably 7 french. Likewise the thickness of the outer wall is not critical, so long as the central lumen 115 can accommodate components extending therethrough. If desired, the inner surface of the outer wall is lined with a stiffening tube 118 to provide improved torsional stability. An example of a catheter body construction suitable for use in connection with the present invention is described and depicted in U.S. Pat. No. 6,064,905, the entire disclosure of which is incorporated herein by reference.

Components that extend from the control handle 116 and into the central lumen 115 of the catheter body 112 include, for example, a one or more puller wires 136 for deflection of the intermediate section 114, lead wires 130 for electrodes, irrigation/inflation tubing 111 with lumen 137, guidewire tubing 119 with lumen 122, and a cable 134 for an electromagnetic position sensor 132 housed in or near the assembly 125.

Figure 6C:
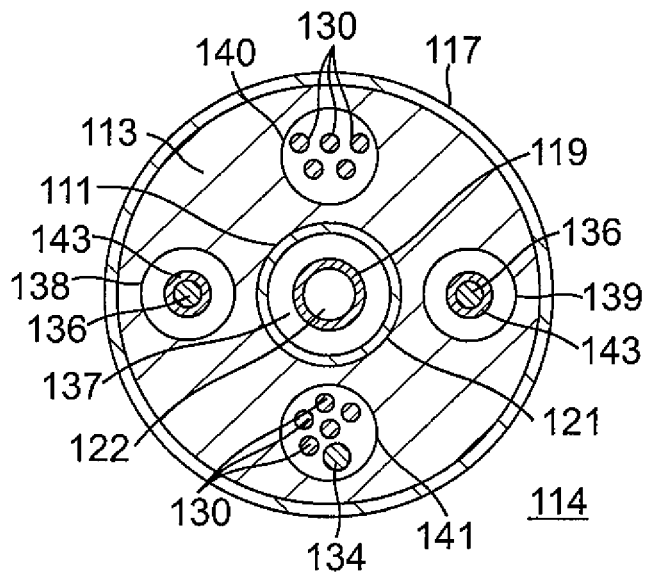
FIG. 6C is an end cross-sectional view of the intermediate deflectable section of FIGS. 6A and 6B, taken along line C-C.

FIGS. 6A, 6B and 6C illustrate an intermediate section 114 in accordance with another embodiment which comprises a shorter section of tubing 113. The tubing has a braided mesh construction with a central lumen 121 and multiple off-axis lumens, for example lumens 138, 139, 140 and 141. Each of diametrically opposing first and second lumens 138 and 139 carries a respective puller wire 136 to enable bi-directional deflection of the catheter. Third lumen 140 carries the lead wires 130 and fourth lumen 141 carries the sensor cable 134. Additional lumens may be provided as needed.

The tubing 113 of the intermediate section 114 is made of a suitable non-toxic material that is preferably only slightly more flexible than the catheter body 112. A suitable material for the tubing 113 is braided polyurethane, i.e., polyurethane with an embedded mesh of braided stainless steel or the like. The size of each lumen is not critical so long as it is sufficient to house the respective components extending therethrough.

The length of the intermediate section 14 is a relatively small portion of the useful length of the catheter, and may range from about 6.35 cm to about 7.62 cm, more preferably about 6.43 cm to about 6.5 cm, and still more preferably about 6.4 cm.

A means for attaching the catheter body 112 to the intermediate section 114 is illustrated in FIGS. 6A and 6B. The proximal end of the intermediate section 114 comprises an outer circumferential notch 142 that receives an inner surface of the outer wall 117 of the catheter body 112. The intermediate section 114 and catheter body 112 are attached by glue or the like.

If desired, a spacer (not shown) can be located within the catheter body 112 between the distal end of the stiffening tube 118 (if provided) and the proximal end of the intermediate section. The spacer provides a transition in flexibility at the junction of the catheter body and intermediate section, which allows this junction to bend smoothly without folding or kinking. A catheter having such a spacer is described in U.S. Pat. No. 5,964,757, the disclosure of which is incorporated herein by reference.

The puller wires 136 carried in the lumens 138 and 139 of the intermediate shaft 14 are preferably coated with Teflon®. The puller wires may be made of any suitable metal, such as stainless steel or Nitinol, or a stronger material such as Vectran® nylon tubing, where the Teflon coating imparts lubricity to the puller wire. Each puller wire may have a diameter ranging from about 0.006 to about 0.010 inch.

As shown in FIG. 6B, each puller wire 136 passes through a respective compression coil 143 in surrounding relation to its puller wire. The compression coil 143 extends generally from the proximal end of the catheter body 112 to the proximal end of the intermediate section 114 and may be secured at their proximal and distal ends respectively to the stiffening tube 118 and the proximal end of the tubing 113 by glue joints (not shown). The compression coil 143 is made of any suitable metal, preferably stainless steel, and is tightly wound on itself to provide flexibility, i.e., bending, but to resist compression. The inner diameter of the compression coil is preferably slightly larger than the diameter of the puller wire. Within the catheter body 112, the outer surface of the compression coil 143 is also covered by a flexible, non-conductive sheath 144, e.g., made of polyimide tubing. Within the intermediate section 114, each puller wire extends through a protective sheath 145 to prevent the puller wire from cutting into the tubing 113 of the intermediate section 114 during deflection.

Proximal ends of the puller wires 136 are anchored in the control handle 116. Distal ends of the puller wires are anchored in or near the distal end of the tubing 113 of the intermediate section 114. As illustrated in FIG. 6B, a T-shaped anchor is formed, which comprises a short piece of tubular stainless steel 146, e.g., hypodermic stock, which is fitted over the distal end of the puller wire and crimped to fixedly secure it to the puller wire. The distal end of the tubular stainless steel 146 is fixedly attached, e.g., by welding, to a cross-piece 147 formed of stainless steel ribbon or the like. The cross-piece 147 extends through a hole (not shown) formed in the tubing 113 and because the cross-piece 147 is larger than the hole and, therefore, cannot be pulled through the hole, the cross-piece 147 anchors the distal end of the puller wire to the distal end of the intermediate section 114.

Extending through the center lumen 121 of the tubing 113 of the intermediate section 114 is the irrigation/inflation tubing 111 with lumen 137. The guidewire tubing 119 is inside of and extends through the lumen 137 of the tubing 111. Proximal ends of the tubings 111 and 119 are connected to a connecting member with ports similar to those shown in FIG. 1. One port is adapted for connection to a pressurizeable irrigation/inflation medium source and a pump (not shown). The other port is adapted to receive a guidewire (not shown).

At a distal end of the intermediate section 114, the balloon electrode assembly 125 is arranged. The balloon electrode assembly 125 has a structure similar to the aforementioned balloon electrode assembly 25, as described above. The balloon electrode assembly 125 includes an outer balloon member 123, an inner balloon member 124, and a plurality of electrodes mounted on an outer surface of the outer balloon member 123. However, with the multi-lumened tubing 113 of the intermediate section 114 extending from the catheter body 112 to the assembly 125, proximal opening 124P of the inner balloon member 124 is inserted in a distal end of the central lumen 121 of the tubing 113 and sealed to an inner surface of the central lumen 121. Proximal opening 123P of the outer balloon member 123 is mounted and sealed around an outer surface of the distal end of the tubing 113.

The guidewire tubing 119 extends through the lumen of the irrigation/inflation tubing 111, the central lumen 121 of the tubing 113 of the intermediate section 114 and cavity C124 of the inner balloon member 124. The tubings 119 and 111 are relatively sized such that irrigation and/or inflation medium can flow sufficiently unimpeded in lumen 137 of the tubing 111 along the length of the catheter to the balloon electrode assembly 125. As described above, the balloon members 123 and 124 are constructed of a flexible and compliant material, which may be elastic or nonelastic, that allows the members to inflate and deflate. The internal force is provided by introduction of the inflation medium into cavity C124 of the inner balloon 124.

FIGS. 10, 10A and 10B illustrate an intermediate section 414 and a balloon assembly 425 in accordance with another embodiment. The catheter body 412 has a multi-lumen tubing 413 structured much like the tubing 113 of FIGS. 6A and 6B. The tubing 413 has one or more additional lumens, for example, diametrically opposed, off-axis lumens 457 for transport of irrigation fluid along the intermediate section 414. Irrigation fluid is fed into each lumen 457 at a proximal end of the tubing 413 by a respective irrigation tubing (not shown) that extends through a catheter body (not shown) connected to the intermediate section 114. At a distal end of the tubing 425, each lumen 457 is in communication with a space S between outer and inner balloon members 423 and 424. Formed in the outer balloon member 424 are irrigation fluid ports 456 that allow irrigation fluid entering the space S to exit to outside the outer balloon member 423.

FIG. 10B illustrates one or more spacers 455 positioned between the inner surface of the outer balloon member 423 and the outer surface of the inner balloon member 424. The spacers may be affixed to the inner surface of the outer balloon and/or the outer surface of the inner balloon member. The spacers 455 are adapted to provide fluid passage gaps or channels between the inner and outer balloon members so that fluid can distribute between the inner and outer balloon members and not be trapped or have flow impeded in any particular area if the balloon members are pressed against each other. The spacers can be of any suitable overall shape or configuration with any suitable cross-sectional shape or configuration. They may be more of a block shape or an elongated shape (extending in the longitudinal direction). In the illustrated embodiment, the spacers have a trapezoidal cross-sectional shape with a greater width in contact with the outer surface of the inner balloon member 424 and a lesser width in contact with the inner surface of the outer balloon member 425 to better ensure the formation of sizable fluid passage gaps between the balloon members 423 and 424 during expansion and/or when pressed against tissue. It is understood that either one or both of the inner surface of the outer balloon member and the outer surface of the inner balloon member may also be formed with grooves to ensure fluid distribution.

In accordance with a feature of the present invention, irrigation fluid and its path throughout the catheter is kept separate and isolated from inflation medium and its path throughout the catheter. In the latter regard, inflation medium is delivered to the inner balloon member 424 via structures similar to those described for the catheter of FIGS. 6A, 6B and 6C. In the illustrated embodiment, an inflation medium tubing 411 extends through the catheter body and continues through a lumen 421 in the tubing 413 which feeds into a cavity of the inner balloon member 424.

Figure 7:
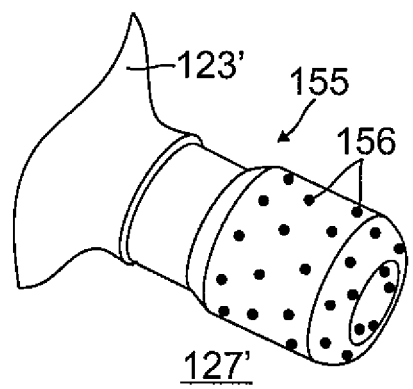
FIG. 7 is a perspective view of a distal electrode assembly of the present invention, in accordance with another embodiment.
Figure 7A:
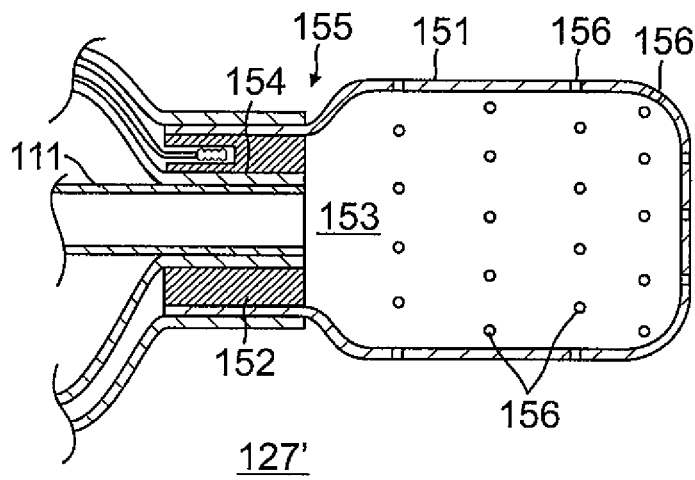
FIG. 7A is a side cross-sectional view of the distal electrode assembly of FIG. 7.

FIGS. 7 and 7A illustrate a distal assembly 127' in accordance with another embodiment, having an irrigated tip electrode 155. The distal assembly may be used with a catheter wherein an irrigation tube 111 generally replaces the guidewire tube 19 of FIG. 2 or 119 of FIG. 6A. The tip electrode 155 has a two-piece construction that includes an electrically-conductive dome shell 151 and an electrically-conductive plug member 152 which define a cavity of an internal plenum chamber 153 that is surrounded and enclosed by the shell 151 and the plug member 152. The shell 151 has a domed atraumatic distal end adapted for tissue contact and an open proximal end that is generally sealed by the plug member 152. Formed in the side wall of the shell are a plurality of fluid ports 156 that allow fluid communication between the chamber 153 and outside the shell 151.

The plug member 152 is formed with a through-hole 154 that receives a distal end of the irrigation tube 111. Thus, the tube 111 provides fluid, e.g., saline, that passes through a catheter body, an intermediate section, if any, and a balloon assembly, and into the tip electrode 155 for cooling the tip electrode. In this embodiment, the fluid that passes through the tube 111 travels separately from the inflation medium passing through the lumen 21 of the inner tube 18 of FIG. 2 or the lumen 137 of the tube 111 of FIG. 6A.

Figure 8:
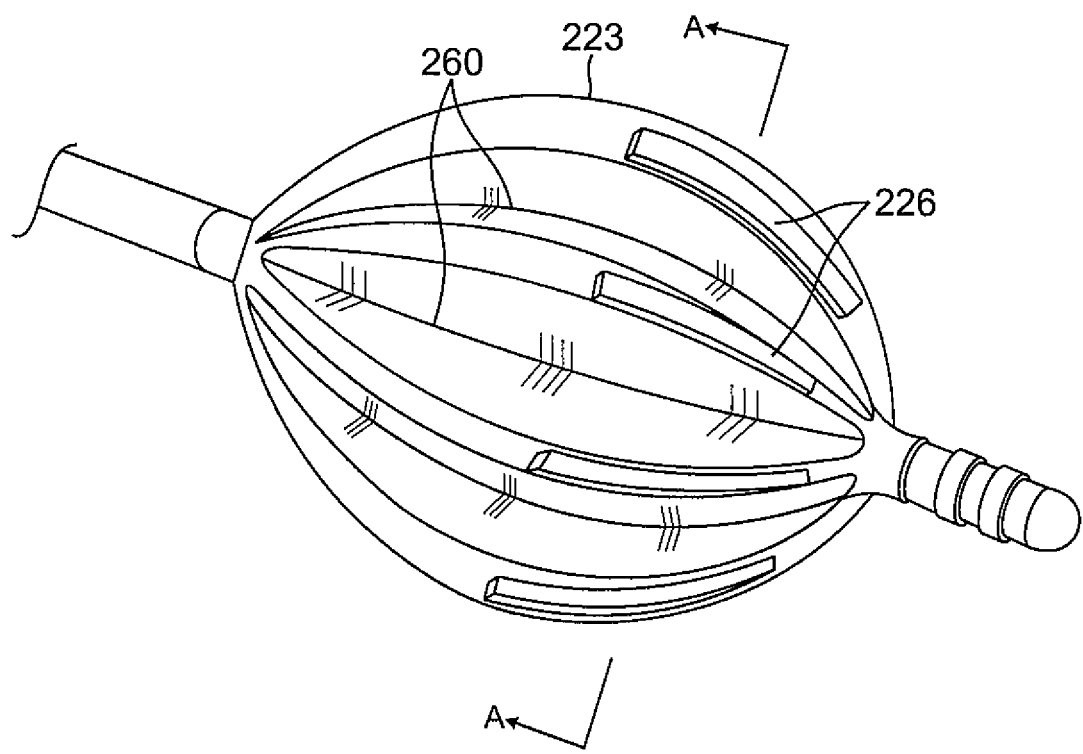
FIG. 8 is a perspective view of a semi-inflated/expanded balloon electrode assembly of the present invention, in accordance with another embodiment.
Figure 8A:
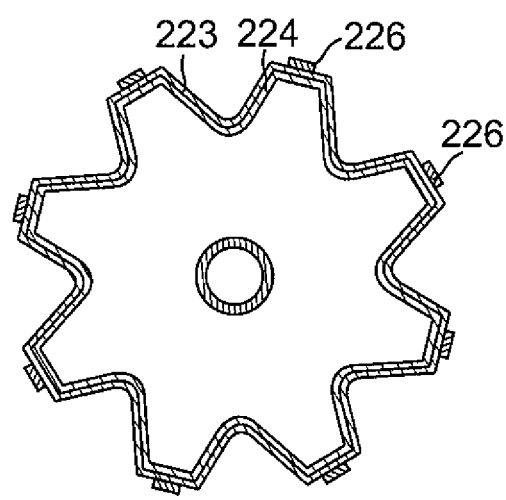
FIG. 8A is an end cross-sectional view of the balloon electrode assembly of FIG. 8, taken alone line A-A.

With reference to FIG. 4, the electrodes 26 that may be carried on any of the balloon assemblies described herein have a generally rectangular and convex configuration with a raised profile relative to the outer surface of the balloon member. However, it is understood that the electrodes may have any suitable configuration, including an elongated form arranged longitudinally with the longitudinal axis of the assembly, as shown in FIGS. 8 and 8A. In that regard, inner and outer balloon members 223 and 224 may have longitudinal pleats or folds 260 extending between elongated electrode strips 226 to facilitate the balloon members collapsing in a more predictable and organized manner. Each electrode strip extends longitudinally or axially on the distal half of assembly 225. The pleats 260 and the electrode strips 226 are spaced apart from each other so neither interferes with the structure or function of the other.

It is understood that each balloon electrode or electrode strip, ring electrode and/or distal tip electrode is connected to an ablation energy source by a respective lead wire. The ablation energy source is adapted to selectively energize each electrode as needed or desired.

FIGS. 9 and 9A illustrate an embodiment of an irrigated balloon electrode assembly 325 with electrodes 326 on the surface of a single or outer balloon member 323. Proximal opening 323P of the member 324 is mounted on a distal end of a multi-lumened tubing 313 of an intermediate deflectable section 314. In the disclosed embodiment, the tubing 313 has a center lumen 321, and four off-axis lumens 338, 339, 340 and 341. Lead wires 330 for the balloon electrodes 326 and any other electrodes of a distal electrode assembly 325 extend through the center lumen 321. Puller wires 336 for bidirectional deflection extend through lumens 338 and 339. Fluid for both inflation and irrigation flow through one or both of lumens 340 and 341.

Side wall of the balloon member 323 may be porous or formed with irrigation ports 372. When the fluid enters the cavity of the balloon member 323, the balloon member expands and the fluid exits the balloon member through irrigation ports 372 to cool the balloon electrodes 326. The ports 372 are positioned in generally close proximity to the electrodes 326. It is understood that adaptations may be made to allow the fluid to also pass into the distal tip assembly for cooling any ring electrodes and/or distal tip electrode.

A protective and support tubing 319 is provided between the intermediate deflectable section 314 and the distal electrode assembly 327. The tubing extends through the cavity of the balloon member. A proximal end is received in the central lumen 321. Apertures 373 are formed in side wall of the tubing 319 so that the lead wires can pass from inside the tubing 319 to their respective electrodes 326. The apertures may be sealed with glue or sealant to prevent leakage of fluid from the cavity into the lumen of the tubing 319. In that regard, distal openings of the lumens 338 and 339 carrying the puller wires are also sealed with glue or sealant to prevent the fluid from entering those lumens.

Figure 11:
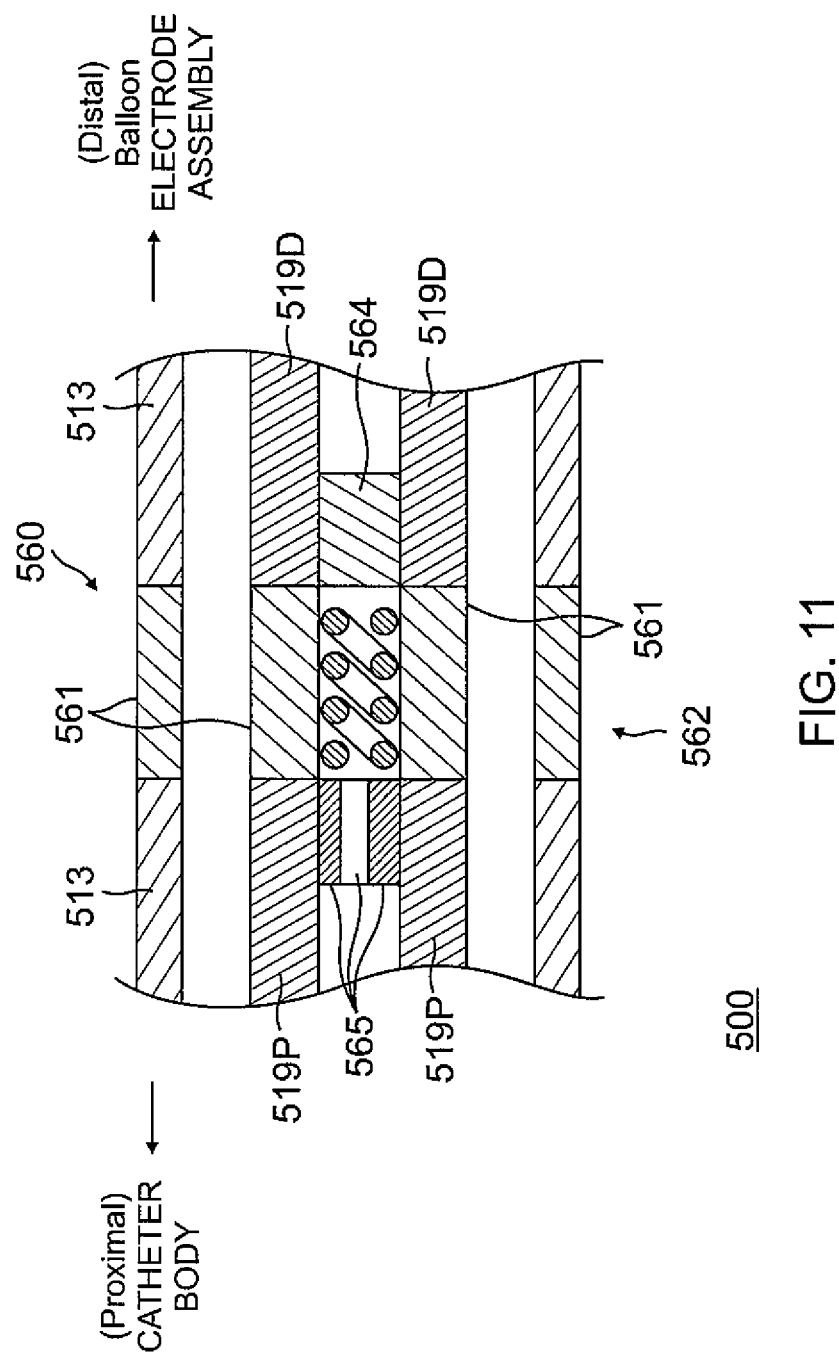
FIG. 11 is a side cross-sectional view of a representing catheter section housing a pressure sensing assembly, in accordance with a feature of the present invention.

The present invention also includes a catheter employing pressure-sensing in its distal portion. FIG. 11 illustrates an embodiment of a catheter section 500 representative of a catheter body or deflectable intermediate section proximal of a balloon electrode assembly. The catheter section 500 has many structural similarities to the aforementioned catheter body and intermediate section of FIGS. 4A, 4B, 6A and 6B. Whether the section 500 comprises multiple coaxial tubings or a multi-lumen tubing 513, it has a center tubing or center portion of a tubing 519 that defines a center on-axis lumen which houses a pressure sensing assembly 560 at or near the distal end of the tubing 519. As illustrated in FIG. 11, the pressure sensing assembly 560 is embodied in a joint 562 generally between distal portion 519D and proximal portion 519P. The joint 562 is formed by a short section of a flexible tubing 561 that is configured similarly to the tubing 519, with at least one lumen that connects the center on-axis lumen of 519. There may be other lumens or passages that correspond and are axially aligned with other lumens or passages of the tubing 519. The tubing 561 may be constructed of a material adapted to permit unimpeded bending and compression of the joint. The tubing 513 is relatively rigid, by comparison with the tubing 561.

The joint 562 includes a resilient member 563 that may take the form of, for example, a coil spring, but other types of resilient components may alternatively be used for this purpose. Resilient member 563 permits a limited range of relative movement between balloon electrode assembly 525 and the intermediate section 514 in response to forces exerted on the balloon electrode assembly, such as when the latter comes into contact with tissue.

Distal of the resilient member 563, a magnetic position sensor 564 is housed in the lumen of the tubing 519 (preferably centered and on-axis in the intermediate section 514. Sensor 564 may comprise one or more miniature coils, and typically comprises multiple coils oriented along different axes. Proximal of the resilient member 563, a miniature magnetic field generator 565 is housed in the lumen of the tubing 519. Typically, field generator 565 comprises a coil, which is driven by a current conveyed through the catheter. Alternatively, position sensor 564 may comprise either another type of magnetic sensor, an electrode which serves as a position transducer, or position transducers of other types, such as impedance-based or ultrasonic position sensors. Although FIG. 11 shows a single position sensor 564, embodiments of the present invention may utilize more than one position sensors.

As understood by one of ordinary skill in the art, the magnetic field created by field generator 565 causes the coils in sensor 564 to generate electrical signals at the drive frequency of the field generator 565. The amplitudes of these signals will vary depending upon the location and orientation of at least distal portion 519D of the longitudinal tubing 519 extending through balloon electrode assembly 525 relative to intermediate section 14. A calibration processor (not shown) in calibration unit (not shown) processes these signals in order to determine the axial displacement and the magnitude of the angular deflection of the distal portion 519D relative to proximal portion 519P. (Because of the axial symmetry of the field generated by a coil, only the magnitude of the deflection can be detected using a single coil in field generator 565, and not the direction of the deflection. Optionally, field generator 565 may comprise two or more coils, in which case the direction of deflection may be determined, as well. In that regard, the embodiment of FIG. 11 includes three coils). The magnitudes of the displacement and deflection may be combined by vector addition to give a total magnitude of the movement of distal portion 519D relative to proximal portion 519P.

The relative movement of distal portion 519D relative to distal end 14 gives a measure of the deformation of resilient member 563. Thus, the combination of field generator 565 with sensor 564 serves to sense pressure. By virtue of the combined sensing of displacement and deflection, the pressure sensing assembly 560 should read the pressure correctly regardless of whether the pressure is exerted on distal portion 519D or balloon electrode assembly head-on or at an angle. Further details of this position sensor are described in U.S. Pat. Nos. 8,357,152 and 8,535,308, the entire contents of which are hereby incorporated by reference.

The catheter also comprises a non-volatile memory, such as electronically erasable programmable read only memory (E.sup.2PROM), which stores calculation coefficients computed during calibration, as described in U.S. Pat. No. 8,521,462, the entire disclosure of which is hereby incorporated by reference. When the catheter is later used in a medical system, the actual pressure exerted by the catheter's balloon electrode assembly on body tissue can be derived with high accuracy from deflection measurements, using the calibration coefficients stored in memory. It is understood that where the catheter has a distal electrode assembly distal of the balloon electrode assembly, the pressure sensing assembly is adapted to sense the actual pressure exerted by the distal assembly on body tissue.

It is understood that the pressure sensing assembly 560 may be positioned at different locations along the distal portion 519D, including the portion extending between the distal and proximal ends of the balloon electrode assembly. Different positions may vary stability of the balloon electrode assembly when pressed against tissue surface.

To use a catheter of the invention, an electrophysiologist may introduce a guiding sheath and dilator into the patient, as is generally known in the art. A guidewire may also be introduced for a catheter adapted for such use, such as the catheter of FIGS. 2 and 5. A suitable guiding sheath for use in connection with the inventive catheter is the PREFACE™ Braided Guiding Sheath (commercially available from Biosense Webster, Inc., Diamond Bar, Calif.). Where a guidewire is used, it is inserted and then the dilator is removed. The catheter is then introduced through the guiding sheath. The catheter may be introduced to the right atrium via the inferior vena cava. To reach the left atrium, the catheter passes through the septum.

The guiding sheath covers balloon electrode assembly in a collapsed position so that the entire catheter can be passed through the patient's vasculature to the desired location. The compliant material of the balloon member(s) allows the assembly to readily collapse and/or be folded to fit in the guiding sheath. Once the distal end of the catheter reaches the desired location, e.g., the left atrium, the guiding sheath is withdrawn to expose the balloon electrode assembly. The balloon electrode assembly may then be expanded by introduction of inflation fluid into a balloon member. The balloon electrode assembly may be expanded as needed or desired to fit in an ostium or a concave region of the atrium. Circumferential mapping and/or ablation is accomplished by:

(1) inflating the balloon electrode assembly;
(2) nesting or otherwise placing the balloon electrode assembly in the desired location such that atrial tissue contact along a circumference is made with one or more electrodes of the balloon electrode assembly;

(3) activating the one or more electrodes for sensing and/or ablation;
(4) rotating the balloon electrode assembly about its longitudinal axis such that different atrial tissue contact is made generally along the same circumference is made with one or more electrodes of the balloon electrode assembly;
(5) activating the one or more electrodes for sensing and/or ablation;
(6) repeating steps (4) and (5) as desired;
(7) deflating the balloon electrode assembly; and
(8) activating one or more electrodes on the distal electrode assembly for sensing and/or ablation.

It is understood that the aforementioned steps or acts may be performed in the order set forth above, or in another order as needed or appropriate. Any one or more of the aforementioned steps may be performed for mapping, ablation and/or validation.

Through known methods such as impedance, temperature and/or contact force measurements, the electrophysiologist can determine which electrode(s) are in contact with atrial tissue. With a fully integrated multi-electrode platform, such as provided by the nMARQ Generator available from Biosense Webster, Inc., which allows simultaneous activation of selected electrodes, mapping, ablation and validation can be performed with the use of a single catheter with greater efficiency and less complexity.

As recognized by one skilled in the art, the balloon electrode assembly can be fully or partially inflated. With bidirectional deflection, the catheter can be maneuvered to position the balloon electrode assembly and the distal electrode assembly in or near an ostium or a pulmonary vein. Using the electrodes on the assemblies in combination with the location sensor, the electrophysiologist can map local activation time, ablate and validate, which can guide the electrophysiologist in diagnosing and providing therapy to the patient. Accordingly, the electrophysiologist can visualize each electrode on a 3-D mapping system so the electrophysiologist knows where each electrode is in the patient's anatomy when the balloon members are inflated. Each electrode may also be equipped with temperature feedback, e.g., by means of thermistors or thermocouples.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention. As understood by one of ordinary skill in the art, the drawings are not necessarily to scale. Also, different features of different embodiments may be combined as needed or appropriate. Moreover, the catheters described herein may be adapted to apply various energy forms, including microwave, laser, RF and/or cryogens. Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter comprising:
an elongated catheter body having proximal and distal ends;
a first assembly distal of the catheter body, the first assembly having a balloon assembly comprising an outer balloon member with an outer surface and an inner balloon member configured to be at least partially covered by the outer balloon member, the outer balloon member having at least one outer fluid port configured to allow fluid to pass from a space between the outer balloon member and the inner balloon member to the outer surface of the outer balloon member, the balloon assembly further comprising multiple ablation electrodes on the outer surface of the outer balloon member;
a tubing extending through the catheter body, the tubing defining a lumen adapted to pass the fluid into the inner balloon member to expand the inner balloon member;
a second assembly distal of the first assembly, the second assembly having at least one electrode and an electromagnetic position sensor;
a cable disposed in the space between the outer balloon member and the inner balloon member and connected to the electromagnetic position sensor;
a plurality of lead wires disposed in the space between the outer balloon member and the inner balloon member and connected to the multiple ablation electrodes.

2. The catheter of claim 1, further comprising a pressure sensing assembly.

3. The catheter of claim 2, wherein the pressure sensing assembly is located proximal of the balloon assembly.

4. The catheter of claim 2, wherein the pressure sensing assembly is located between a distal end and a proximal end of the balloon assembly.

5. The catheter of claim 1, wherein the multiple ablation electrodes on the outer surface of the outer balloon member are elongated and positioned along a longitudinal axis of the catheter.

6. The catheter of claim 1, wherein the at least one electrode of the second assembly includes an irrigated tip electrode.

7. The catheter of claim 1, wherein the at least one electrode of the second assembly includes a ring electrode.

8. The catheter of claim 1, wherein the fluid includes an inflation fluid configured to be delivered to the inner balloon member.

9. The catheter of claim 1, wherein the fluid includes an irrigation fluid configured to be delivered to the space between the inner balloon member and the outer balloon member.

10. A catheter comprising:
an elongated catheter body having proximal and distal ends;
a balloon electrode assembly distal of the catheter body, the balloon electrode assembly having at least an inner balloon member and an outer balloon member covering at least a portion of the inner balloon member, the balloon electrode assembly further comprising multiple ablation electrodes on an outer surface of the outer balloon member, and at least one electrode lead wire extending from the multiple ablation electrodes through a space between the inner balloon member and the outer balloon member;
a tubing extending through the catheter body, the tubing defining a lumen adapted to pass the fluid into the inner balloon member for expansion of the inner balloon member;
a distal electrode assembly distal of the first assembly, the distal electrode assembly having at least one electrode and an electromagnetic position sensor;
a cable disposed in the space between the outer balloon member and the inner balloon member and connected to the electromagnetic position sensor, wherein the outer balloon member is adapted for expansion in response to expansion of the inner balloon member.

11. The catheter of claim 10, wherein the outer balloon member has at least one fluid port configured to pass the fluid from the space between the outer balloon member and the inner balloon member to outside of the outer balloon member.

12. The catheter of claim 10, further comprising a pressure sensing assembly.

13. The catheter of claim 12, wherein the pressure sensing assembly is proximal of the balloon electrode assembly.

14. The catheter of claim 12, wherein the pressure sensing assembly is between a distal end and a proximal end of the balloon electrode assembly.

15. The catheter of claim 12, wherein the pressure sensing assembly has a resilient member.

16. The catheter of claim 10, wherein the at least one electrode of the distal electrode assembly comprises an irrigated tip.

17. The catheter of claim 1, wherein the multiple ablation electrode electrodes are in the form of elongated electrode strips extending longitudinally along the axis of the balloon electrode assembly.

18. The catheter of claim 10, wherein the multiple ablation electrodes are in the form of elongated electrode strips extending longitudinally along the axis of the balloon electrode assembly, and wherein the inner balloon member and the outer balloon member include longitudinal pleats extending between the elongated electrode strips.

19. The catheter of claim 10, further comprising a sensor including at least two coils oriented along different axes.

20. The catheter of claim 19, further comprising a magnetic field generator.

21. A catheter comprising:
an elongated catheter body having proximal and distal ends;
a first assembly distal of the catheter body, the first assembly having a balloon assembly comprising an outer balloon member with an outer surface and an inner balloon member configured to be at least partially covered by the outer balloon member, the outer balloon member having at least one outer fluid port configured to allow fluid to pass from the space between the outer balloon member and the inner balloon member to the outer surface of the outer balloon member, the balloon assembly further comprising multiple ablation electrodes on the outer surface of the outer balloon member, the multiple ablation electrodes connected to an ablation energy source;
a tubing extending through the catheter body, the tubing defining a lumen adapted to pass the fluid into the inner balloon member to expand the inner balloon member;
a second assembly distal of the first assembly, the second assembly having at least one electrode and an electromagnetic position sensor;
a cable disposed in the space between the outer balloon member and the inner balloon member and connected to the electromagnetic position sensor; and
a plurality of lead wires disposed in the space between the outer balloon member and the inner balloon member and connected to the multiple ablation electrodes.

22. The catheter of claim 21, further comprising a plurality of spacers disposed between an inner surface of the outer balloon member and an outer surface of the inner balloon member.

23. The catheter of claim 21, wherein the plurality of spacers are affixed to the inner balloon member.

24. The catheter of claim 21, wherein the plurality of spacers are affixed to the outer balloon member.

* * * * *